(12) United States Patent
Hirashima

(10) Patent No.: US 8,541,641 B2
(45) Date of Patent: Sep. 24, 2013

(54) AID FOR PREVENTION OF WOUND DEHISCENCE

(75) Inventor: Toshifumi Hirashima, Shizuoka (JP)

(73) Assignee: Yugenkaisha Choryu, Kosai-Shi, Shizuoka (JP)

( * ) Notice: Subject to any disclaimer, the term of this patent is extended or adjusted under 35 U.S.C. 154(b) by 0 days.

(21) Appl. No.: 13/258,779

(22) PCT Filed: Jun. 3, 2011

(86) PCT No.: PCT/JP2011/062767
§ 371 (c)(1),
(2), (4) Date: Aug. 21, 2012

(87) PCT Pub. No.: WO2012/014567
PCT Pub. Date: Feb. 2, 2012

(65) Prior Publication Data
US 2012/0310132 A1    Dec. 6, 2012

(30) Foreign Application Priority Data

Jul. 29, 2010 (JP) .................................. 2010-169950
Dec. 9, 2010 (JP) .................................. 2010-274442
Apr. 5, 2011 (JP) .................................. 2011-083394

(51) Int. Cl.
*A61F 13/00* (2006.01)
*A61B 17/08* (2006.01)

(52) U.S. Cl.
USPC .................. 602/42; 602/43; 602/79; 606/213; 606/215; 606/216

(58) Field of Classification Search
USPC ............. 602/41–59; 606/213–216; 128/888, 128/889
See application file for complete search history.

(56) References Cited

U.S. PATENT DOCUMENTS 3,103,218 A * 9/1963 Ajemian .......................... 602/79
2008/0033334 A1  2/2008 Gurtner et al.
2011/0004173 A1  1/2011 Hu et al.

FOREIGN PATENT DOCUMENTS

| DE | 10 2009 020 763 A1 | 11/2009 |
| JP | 6-44511 U | 6/1994 |
| JP | 2009-545382 A | 12/2009 |
| WO | 2006/124671 A2 | 11/2006 |
| WO | 2009/049232 A1 | 4/2009 |

* cited by examiner

*Primary Examiner* — Kim M Lewis
(74) *Attorney, Agent, or Firm* — McDermott Will & Emery LLP

(57) ABSTRACT

A dehiscence preventive member is adapted to cover up a wound and surrounding tissues. A plurality of holding members are adapted to hold the dehiscence preventive member closely upon the wound and the surrounding tissues, and a contraction preventive member keeping the dehiscence preventive member suitably expanded in a dehiscence direction and of preventing the expanded dehiscence preventive member from contracting. The contraction distance of the dehiscence preventive member in the dehiscence direction is equal to or greater than a contraction distance of the holding member in the dehiscence direction. The dehiscence preventive is closely applied to the wound and surrounding tissues after expansion in the dehiscence direction such that the contraction distance of the dehiscence preventive member in the dehiscence direction is equal to or greater than the contraction distance of the dehiscence preventive member in a direction normal to the dehiscence direction.

3 Claims, 4 Drawing Sheets

AID FOR PREVENTION OF WOUND DEHISCENCE

CROSS REFERENCE TO PRIOR APPLICATIONS

This application is a U.S. National Phase application under 35 U.S.C. §371 of International Application No. PCT/JP2011/062,767, filed on Jun. 3, 2011 and claims benefit of priority to Japanese Patent Application No. 2010-169950, filed on Jul. 29, 2010; Japanese Patent Application No. 2010-274442, filed on Dec. 9, 2010; and Japanese Patent Application No. 2011.-083394, filed on Apr. 5, 2011. All these applications are herein incorporated by reference.

TECHNOLOGY FIELD

The present invention relates to an aid for prevention of wound dehiscence, which is a rupture or splitting open of a wound.

BACKGROUND TECHNOLOGY

The word "wound" is a general term for injury inflicted upon a part of a body, and a wound can be generally classified into two kinds: an "incised wound" which refers to any of open wounds caused by cutting with a sharp material such as a knife; a "blunt wound" which refers to any of closed wounds without rupture of skin caused by hitting with a blunt object such as a blunt weapon.

Conventionally, when the wound is an "incised wound" which is an open wound, its dehiscence is prevented by means of closing and holding the wound with adhesive plaster or roll bandage or something like that when the wound is shallow, and in the case of a deep wound, the dehiscence is prevented by closing the wound by means of suturing with suture thread and the like. Further, in the case of the means of suturing with suture thread, in order to prevent the dehiscence that may be caused by breaking of the suture thread by external force or the like, it has been generally practiced that a more conservative choice is made in selecting from a plurality of suture threads having appropriate thicknesses.

However, a use of a thick suture thread is apt to leave a more conspicuous trace of suture operation, so that it is not a preferable practice. Also when a thick suture thread is used and thereby the skin tissue surrounding the wound is over-forced to gather over the wound with the stitches, the circulation of the blood and the like through the tissues surrounding the sutured wound would become insufficient, whereupon the tissues surrounding the sutured wound gradually undergo necrosis and a dehiscence would result.

Furthermore, in the case of a suturing on the occasion of surgical operation or the like, the tissues surrounding the wound must be gathered toward the wound. For this reason, the suture thread and the tissues surrounding the wound tug each other. Under this situation, when an external force is imparted the suture thread, if it is thin, would break, and, if it is thick, the tissues surrounding the wound would rupture. In other words, even if a suture thread of a suitable thickness is selected, it has been sometimes difficult to prevent dehiscence.

Among some surgeons, a use of a padding implement is proposed in order to appease the pains to the patient through prevention of dehiscence and distortion of the stitched skin caused by suture thread as well as necrosis (for example, see Publication-in-IP 1).

Publication-in-IP 1 proposes a padding implement for prevention of dehiscence wherein the padding implement is disposed to have a large area to contact the wounded part so as to avoid concentration of stress at the wounded tissues, and it is shaped in a manner such that it is able to impart tension to the thread, and it is formed with a guide slit for rendering the thread winding easy and with a thread fixing slit.

However the padding implements for prevention of dehiscence such as the one mentioned above require mastering of the technique for the use of the dehiscence prevention padding implements before the surgical operation wherein the padding implement is applied during the suture. Also it is necessary to detach and attach the padding implement whenever the padding implement is to be disinfected and the wounded part is to be dried, and the technique for this detachment and attachment work must also be mastered beforehand. Furthermore, the patient must be willing to lead a life wherein he or she has to watch out for the external forces that may come to the dehiscence prevention padding implement applied to the sutured area, especially for the force inflicted when the patient turns round in bed while asleep or the like. Also, there are scarce number of books and theses that discourse upon the remedy of dehiscence scientifically, and the current situation is that there are no established methods for the remedy and the prevention of it. Especially in the case of dehiscence caused by the necrosis of the tissues surrounding the sutured wound resulting from poor circulation of blood or the like, no good result is expected from re-suturing, and it is not a rare case wherein the surgeon cannot help but resort to the classical remedy of removing all the sutured threads, excising the necrotic tissues, covering the wound with a wound dressing, and expecting for a natural healing; hence the patient is not infrequently forced to be hospitalized or continue visiting the hospital for a long time. Therefore it has not been an easy thing to prevent dehiscence itself and to use and manipulate the conventional aids for prevention of dehiscence to avoid dehiscence, and the current situation is that there has been no such means as to solve these disadvantages.

PRIOR ARTS

Publications-in-IP

Publication-in-IP 1:
Japanese Published Utility Model Application No. H06-44511

SUMMARY OF THE INVENTION

Problems the Invention Seek to Solve

It is an object of the present invention to provide an aid for prevention of wound dehiscence, and in particular a kind that is highly effective in preventing the dehiscence of an incised wound inflicted on a body by cutting, and that is easy to use and manipulate.

Means to Solve the Problems

In order to solve the above mentioned problems, the present inventors researched vigorously and came to complete the invention. In the upshot, the present inventive aid for prevention of wound dehiscence is a device aid for preventing the closed cut wound from splitting open and this is accomplished by applying this aid device to cover up the wound and its surrounding tissues; and this device comprises a dehiscence preventive member adapted to cover up the wound and the wound-surrounding tissues and a plurality of a holding member adapted to hold the dehiscence preventive member closely upon the wound and the wound-surrounding tissues, and a plurality of contraction preventive member capable of keeping the dehiscence preventive member suitably expanded in the direction of dehiscence and of preventing the expanded dehiscence preventive member from contracting; and the device is characterized in that the device is equipped with a function such that a contraction distance of the dehiscence preventive member in the dehiscence direction which (contraction distance) is determined in response to the application of the dehiscence preventive member is equal to or greater than a contraction distance of the holding member in the dehiscence direction which is determined in response to the application of the holding member, and in that the dehiscence preventive member is adapted to be closely applied to the wound and the wound-surrounding tissues after being expanded in the dehiscence direction in a manner such that the contraction distance of the dehiscence preventive member in the dehiscence direction determined in response to the application of the dehiscence preventive member is equal to or greater than the contraction distance of the dehiscence preventive member in a direction normal to the dehiscence direction determined in response to the application of the dehiscence preventive member, and that the contraction preventive member is removed after the dehiscence preventive member is applied by being fixed with the holding member.

Incidentally, it is possible to apply effectively the present inventive aid for prevention of wound dehiscence irrespective of whether the wound has been sutured or not.

Effect of the Invention

According to the aid for prevention of wound dehiscence of the present invention, since the aid for prevention of wound dehiscence is equipped with a means to reduce persistently the physiological and static tension (hereinafter referred to as "physiological tension"), it is possible, if the wound is shallow, to prevent the dehiscence by slackening the tissues surrounding the wound so as to create mild corrugation and to thereby persistently reduce the physiological tension working on the tissues surrounding the wound in the direction of dehiscence (hereinafter referred to as "dehiscence direction"), and it is also possible, if the wound is deep, to prevent the dehiscence, after suturing the wound with suture thread or the like, by slackening the tissues surrounding the sutured wound so as to create mild corrugation and to thereby persistently reduce the physiological tension working on the tissues surrounding the wound in the dehiscence direction and the tension which accompanies the physiological tension and works on the suture thread, so that the wound dehiscence caused by the necrosis of the tissues surrounding the sutured wound triggered by the suture thread preventing the blood and the like from sufficiently circulating through the tissues surrounding the sutured wound is prevented. Furthermore, thanks to the invention, it will be possible to select a thinner suture thread from among the suture threads of various appropriate thicknesses, and as the result the marks of suture left will become less conspicuous. On top of this, it will be possible to dispense with suture operation depending on the situation of the wound. With the present invention, it will also be possible to look to the possibility of prevention of the wound dehiscence of such wounds that are generally difficult to suture such as contused wound and bite wound. Furthermore, with the invention it is possible to maintain the wound and the tissues surrounding the wound in rest, whether the wound is sutured or not, so that the spontaneous recovery may be expedited.

Further, by providing in the inventive aid the contraction preventive member equipped with the function of maintaining the dehiscence preventive member in a state of expansion in the dehiscence direction and of preventing it from contracting, it is possible to maintain the dehiscence preventive member in the state of expansion in the dehiscence direction so that the application of the aid is very easy. In addition to this, by removing the contraction preventive member after being fixed by the holding members, it is possible to allow the dehiscence preventive member to effectively contract in the direction opposite to the dehiscence direction, so that the inventive aid functions as an aid to prevent the wound dehiscence. Also, it is possible to employ the inventive aid for prevention of wound dehiscence effectively whether or not the wound has been sutured.

EXAMPLES TO EMBODY THE INVENTION

Figure 1:
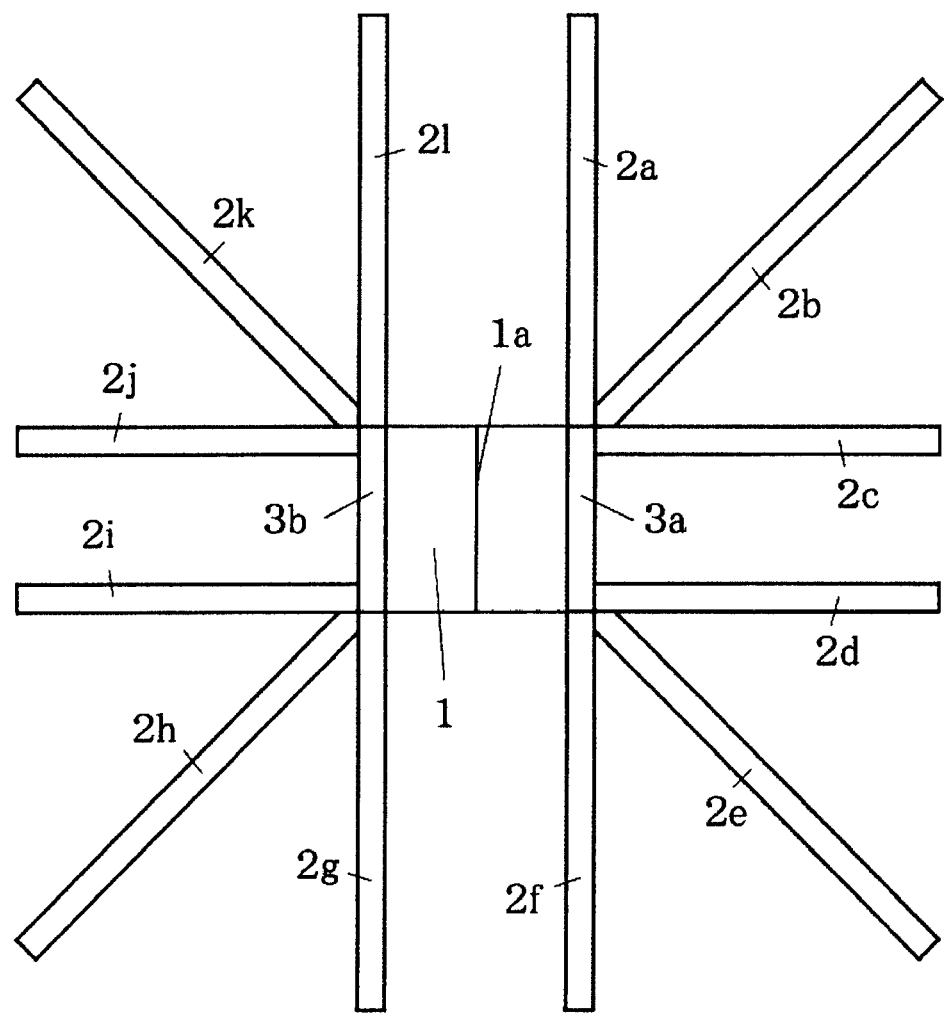
FIG. 1 is a schematic top plan view of an aid for prevention of wound dehiscence according to Example 1 of the present invention, seen as of the time before being applied to the wound.

The present inventors, as they vigorously continued research work, came to know that one of the causes for the wound dehiscence is closely related to a physical force which accompanies the physiological development of the body. For example, a muscle is constantly under the influence of the physiological tension created by the elasticity of the muscle film and the muscle fibers underneath the film and the like, and a skin is constantly under the influence of the physiological tension created by the elasticity of the skin and the muscle organism underneath the skin and the like. It is because of the fact that the sutured muscle and skin are under a constant influence of a physiological tension working in the dehiscence direction that there is a necessity to pull in the muscle and skin to be sutured with the suture thread and the surgeon's thumbs and fingers or with a device or the like, and that after the suture the dehiscence is apt to occur even without a help of an external force.

Therefore, in order to prevent the dehiscence after suturing, it is important to persistently weaken the physiological tension working on the tissues surrounding the wound and the suture thread in the dehiscence direction. Also, in order to expedite the spontaneous recovery after the suture, it is also necessary to maintain the tissues surrounding the wound in rest. However, the tissues surrounding the wound are under the constant influence of the physiological tension in the dehiscence direction so that it is difficult to maintain them in rest.

Now, to slacken toward the sutured wound the tissues surrounding the wound which is sutured to be pulled in a direction opposite to the dehiscence direction, so as to create mild corrugation and to thereby persistently reduce the physiological tension working on the tissues surrounding the wound in the direction of dehiscence and the tension which accompanies the physiological tension and works on the suture thread, is an effective means for prevention of the dehiscence caused by breaking of the suture thread after the suture or of the dehiscence caused by the necrosis or the like of the tissues surrounding the sutured wound owing to the suture thread restricting the circulation.

Through incorporation of this means, as a function, into an aid for to prevention of wound dehiscence, it becomes possible to persistently reduce the physiological tension working, in the dehiscence direction, on the tissues surrounding the sutured wound and the tension accompanying the physiological tension and working on the suture thread, whereby it becomes possible to prevent the dehiscence caused by breaking of the suture thread after the suture or the dehiscence caused by the necrosis or the like of the tissues surrounding the sutured wound owing to the suture thread restricting the circulation.

Furthermore, as it is possible to persistently reduce the physiological tension in the dehiscence direction, it also becomes possible to dispense with suture depending on the state of the wound, so that it is also possible to look to the possibility of prevention of the wound dehiscence of such wounds that are generally difficult to suture such as contused wound and bite wound. In addition, it becomes possible to maintain the tissues surrounding the wound in rest, whether the wound is sutured or not, so that the spontaneous recovery may be expedited From the viewpoint of these, it is realized that the conventional aids for prevention of wound dehiscence have been designed without giving a consideration to the physiological tension working on the tissues surrounding the sutured wound and the suture thread in the dehiscence direction.

Based on this, the inventors came to possess an idea of fabricating a wound dehiscence preventive aid using an elastic material which can be used for medical applications as the material for making the wound dehiscence preventive aid and also using a material having such an elasticity that can outdo the physiological tension, in order to provide a wound dehiscence preventive aid equipped with a function of persistently reducing the physiological tension working on the tissues surrounding the sutured wound in the dehiscence direction and the tension which accompanies the said physiological tension and works on the suture thread—and hence completed the invention.

A test piece was cut out from the material to make the wound dehiscence preventive aid, and the length of the test piece as it was and the length thereof after it was expanded under a predetermined force were measured. Then the length of the unexpanded test piece was subtracted from the length of the expanded test piece to obtain a length value ("contraction distance"). And in view of the friction between the material and the tissues surrounding the wound as well as in view of the phenomenon that takes place as a result of the difference in this contraction distance among the different parts of the wound dehiscence preventive aid, which difference is caused by the use of various materials having different contraction distances for the parts (the said phenomenon being that, when a dehiscence preventive aid is expanded with a predetermined force before application, a part that has a longer contraction distance expands longer than a part that has a shorter contraction distance. In other words, upon application the part that has the greatest contraction distance contracts most), the inventors came to realize that it is possible to introduce into the dehiscence preventive aid as a function a means to persistently reduce the physiological tension working on the tissues surrounding the sutured wound and the suture thread and to slacken the tissues surrounding the sutured wound, and create corrugation and persistently reduce the physiological tension working on the tissues surrounding the sutured wound in the dehiscence direction and the tension working on the suture thread accompanying the physiological tension and working on the suture thread, to thereby prevent the wound dehiscence and hence the present invention is completed.

Now, the examples of the invention shall be explained in detail with reference to the drawings but the invention shall not be construed to be limited by such examples.

The present invention is basically characterized by being equipped to with a function by which the contraction distance of the dehiscence preventive member in the dehiscence direction input accompanying the application of the dehiscence preventive member is rendered equal to or greater than the contraction distance of the holding members in the dehiscence direction input accompanying the application of the holding members by virtue of appropriate selection and combination of the materials that make up the wound dehiscence preventive aid, and further the present invention is characterized in that the dehiscence preventive member is adapted to be closely applied to the wound and the wound-surrounding tissues after being expanded in the dehiscence direction in a manner such that the contraction distance of the dehiscence preventive member in the dehiscence direction determined in response to the application of the dehiscence preventive member is equal to or greater than the contraction distance of the dehiscence preventive member in a direction normal to the dehiscence direction determined in response to the application of the dehiscence preventive member, and that the contraction preventive member is fixed and applied with the holding member. Now, the contraction distance that is determined or input accompanying the application of the respective members herein referred to means the length which is a result of subtracting from the expanded length of each member of the wound dehiscence preventive aid as expanded by the physiological movements of the body which may occur during the resting after the application (e.g., change in bust or abdominal circumference caused by respiration) the length when the load is removed and the member is unexpanded.

In the present invention, it is indispensable that the inventive aid is equipped with a dehiscence preventive member adapted to cover closely the wound and its surrounding tissues, and a holding member having a function of holding the dehiscence preventive member closely over the wound and its surrounding tissues, and that the contraction distance of the dehiscence preventive member in the dehiscence direction as input accompanying the application of the dehiscence preventive member is equal to or greater than the contraction distance of the holding member in the dehiscence direction as input accompanying the application of the holding member, and it is desired that in the dehiscence direction a non-elastic function is provided so as to increase the difference from the contraction distance of the dehiscence preventive member input accompanying the application of the dehiscence preventive member.

However, it is acceptable to use a holding member having elasticity in the dehiscence direction, so long as the aid is provided with a function of slackening the tissues surrounding the sutured wound, corrugating the tissues mildly, and persistently reducing the physiological tension working on the tissues surrounding the sutured wound in the dehiscence direction and the tension working on the suture thread accompanying the physiological tension, and with a function of preventing the dehiscence. Also, as described above, the present invention is characterized such that the dehiscence preventive member is expanded in the dehiscence direction in a manner such that the dehiscence preventive member is applied closely to the wound and the wound-surround tissues while the construction distance of the dehiscence preventive member in the dehiscence direction input accompanying the application of the dehiscence preventive member is equal to or greater than the contraction distance of the dehiscence preventive member in the direction normal to the dehiscence direction input accompanying the application of the dehiscence preventive member, and that the dehiscence preventive member is fixed and applied by means of the holding member in a manner such that the dehiscence preventive member functions as it tries to contract in the direction opposite to the dehiscence direction by virtue of the contractile force of the dehiscence preventive member. Incidentally, what is meant by a situation that the contraction direction of the dehiscence preventive member in the dehiscence direction input accompanying the application of the dehiscence preventive member is equal to or greater than the contraction distance in the direction normal to the dehiscence direction input accompanying the application of the dehiscence preventive member— what is meant by this—is a situation wherein the contraction distance of the dehiscence preventive member in the dehiscence direction input accompanying the application of the dehiscence preventive member is longer than or at the least not shorter than the contraction distance of the dehiscence preventive member in the direction normal to the dehiscence direction input accompanying the application of the dehiscence preventive member.

Figure 2:
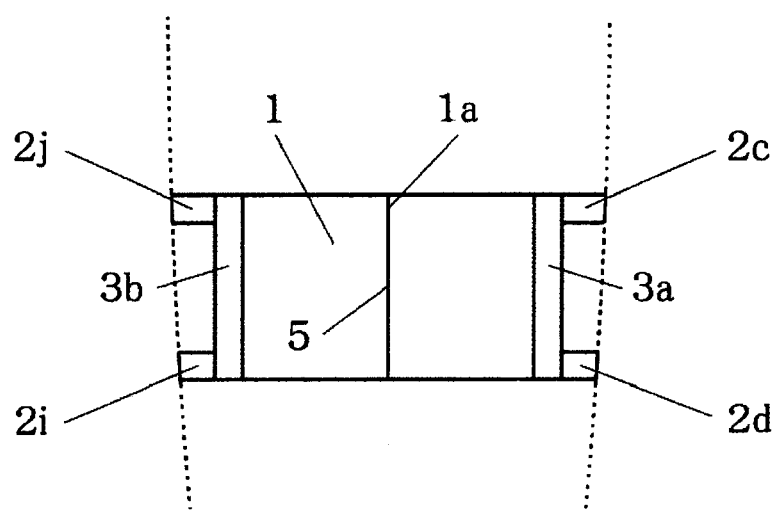
FIG. 2 is a schematic top plan view of the aid for prevention of wound dehiscence of FIG. 1, seen as of the time after it is applied to the wound.

According to Example 1 of the present invention, as shown in FIG. 1 and FIG. 2, the inventive wound dehiscence preventive aid is composed of a dehiscence preventive member 1 adapted to cover up the suture together with the suture-surrounding skin, holding members 2a, 2b, 2c, 2d, 2e, 2f, 2g, 2h, 2i, 2j, 2k, 2l adapted to hold the dehiscence preventive member 1 closely upon the suture and the suture-surrounding skin, and connection sides 3a, 3b for connecting the dehiscence preventive member 1 to the holding members 2a through 2l. As shown in FIG. 1, the holding members 2a through 2l, before application, are connected to and extending from the connection sides 3a, 3b, which are provided on a pair of parallel edges of the dehiscence preventive member 1. The holding members 2a, 2b, 2c, 2d, 2e, 2f are connected to the to connection side 3a and the holding members 2g, 2h, 2i, 2j, 2k, 2l are connected to the connection side 3b.

After application on a forearm, for example, the wound dehiscence preventive aid is, as shown in FIG. 2, fixed with appropriate holding means 2c, 2d, 2i, 2j mostly on the inner side of the forearm to thereby hold the dehiscence preventive member 1 closely on the suture and the suture-surrounding skin in such a manner that by virtue of the contractile force of the dehiscence preventive member 1 the aid functions to prevent dehiscence by contracting in the direction opposite to the dehiscence direction, and the unnecessary holding members 2a, 2b, 2e, 2f, 2g, 2h, 2k, 2l are seen to have been cut away. As the result, preferably, the holding members are positioned in the dehiscence direction, and also are connected at the end portions of the connection sides of the dehiscence preventive member 1 so as to obtain closer holding of the dehiscence preventive member 1 on the suture and the suture-surrounding skin; for example, when the suture 5 coincides with a center line 1a of the dehiscence preventive member 1, the holding members are preferably positioned where the holding members 2c, 2d, 2i, 2j are seen to be positioned in FIG. 2.

Incidentally, in FIG. 1, the reference numeral 1a designates the center line of the dehiscence preventive member 1. In FIG. 2, the situation depicted is such that the wound dehiscence preventive aid is applied with the center line 1a of the dehiscence preventive member 1 lying on the suture 5, which is on the outer side of the forearm, and in order to distinguish the "wound dehiscence preventive aid" from the "human body", the latter is drawn in broken line.

The inventive wound dehiscence preventive aid is equipped with a function to render the contraction distance of the dehiscence preventive member in the dehiscence direction which is input upon the application of the dehiscence preventive member equal to or greater than the contraction distance of the holding members in the dehiscence direction which is input upon the application of the holding members, and the inventive wound dehiscence preventive aid is constructed in a manner such that when the dehiscence preventive member is expanded in the dehiscence direction so as to create a situation in which the contraction distance of the dehiscence preventive member in the dehiscence direction which is input upon the application of the dehiscence preventive member is equal to or greater than the contraction distance of the dehiscence preventive member in the direction vertical to the dehiscence direction which is input upon the application of the dehiscence preventive member, the holding members as applied can fix the wound dehiscence preventive aid in a manner such that the dehiscence preventive member is closely held on the suture and the suture-surrounding skin, and by virtue of the contractile force of the dehiscence preventive member the dehiscence preventive member performs the dehiscence preventive function by trying to contract in the direction against the dehiscence direction, and the holding members are connected via connection means to the end portions of the connection sides of the dehiscence preventive member.

The application of the inventive wound dehiscence preventive aid comprises the following steps: selecting a wound dehiscence preventive aid equipped with a dehiscence preventive member having a suitable size capable of entirely covering up the suture and the suture-surrounding skin, and then positioning the aid such that the center line of the dehiscence preventive member coincides with the suture, and expanding the dehiscence preventive member appropriately in the dehiscence direction, and applying the dehiscence preventive member closely to the suture and the suture-surrounding skin, and selecting appropriate holding members from the twelve holding members that are suitable for holding the dehiscence preventive member closely on the suture and the suture-surrounding skin, and attaching the dehiscence preventive aid by means of the holding members whereby the dehiscence preventive member is rendered to function in a manner such that, by virtue of its contractile force, it is biased to contract in a direction opposite to the dehiscence direction. Thereafter, those holding members not in use are cut away. As a result, some friction occurs, upon the application, between the wound dehiscence preventive aid and the suture and the suture-surrounding skin. Furthermore, the holding members are connected to the end portions of the connection sides of the dehiscence preventive member in such a manner such that such a difference is provided as to cause the contraction distance of the dehiscence preventive member which is input accompanying the application of the dehiscence preventive member, which is closely held on the suture and the suture-surrounding skin, to be equal to or greater than the contraction distance of the holding members which is input accompanying the application of the holding members, and to cause the contraction distance in the dehiscence direction of the dehiscence preventive member which is input accompanying the application to be equal to or greater than the contraction distance in a direction vertical to the dehiscence direction which is input accompanying the application of the dehiscence preventive member, so that the magnitude of the contraction distance which is input accompanying the application of the dehiscence preventive aid is the greatest in the dehiscence direction of the dehiscence preventive member, which is held closely on the suture and the suture-surrounding skin, and thus it is possible to provide the dehiscence preventive aid with the function of slackening the skin surrounding the suture from the direction opposite to the dehiscence direction, and creating mild corrugation and persistently reducing the physiological tension working on the suture thread, the suture, and suture-surrounding skin.

Consequently, upon the application of the wound dehiscence preventive aid, the skin surrounding the suture is allowed to slacken from the direction opposite to the dehiscence direction and thereby it is possible to persistently weaken the physiological tension working on the suture thread, the suture, and the suture-surrounding skin. Therefore, with the wound dehiscence preventive aid according to the present invention, it is possible to input as a function to the wound dehiscence preventive aid the means to persistently reduce the physiological tension working on the wound-surrounding tissues, and it is also possible to slacken the tissues surround the sutured wound, to create mild corrugation, and to persistently reduce the physiological tension working on the tissues surrounding the sutured wound in the dehiscence direction and the tension working on the sutured thread in accompaniment of the said physiological tension, and as the result, it becomes possible to prevent the dehiscence caused by snapping of the suture thread after suturing and also to remedy the defective circulation, caused by the suture thread, of the blood and the like through the tissues surrounding the sutured wound, and thus to contribute to the prevention of the dehiscence owing to the necrosis and the like of the tissues surrounding the sutured wound.

Concretely, in Example 1 embodiment of the present invention, the dehiscence preventive member 1 was made of an elastic Bear Spandex Jersey (cotton 89%, polyurethane 11%), and was used in such a state as of the application that the contraction distance in the dehiscence direction was greater than the contraction distance in the direction perpendicular to the dehiscence direction, and that those sides of the dehiscence preventive member 1 which were perpendicular to the dehiscence direction were folded back double so as to create the connection sides 3a, 3b. Also, the holding members 2a, 2b, 2c, 2d, 2e, 2f, 2g, 2h, 2i, 2j, 2k, 2l were made of twill fabric of cotton yarn which was not elastic, and were of lengths sufficient to suit for an application to a forearm. The holding members 2a, 2b, 2c, 2d, 2e, 2f were sewn to the connection side 3a, and the holding members 2g, 2h, 2i, 2j, 2k, 2l were sewn to the connection side 3b.

Incidentally, in the first embodiment of the present invention, the dehiscence preventive member 1 was made square in shape, and the holding members 2a through 2l were embodied into tapes, but so long as there is provided the function of rendering the contraction distance in the dehiscence direction input accompanying the application of the dehiscence preventive member equal to or greater than the contraction distance in the dehiscence direction input accompanying the application of the holding members, it is possible to shape the dehiscence preventive member 1 in rectangle, circle, lozenge, etc., depending on the application. Also, the holding members 2a through 2l may be as many as and the as lengthy as desired, and may be elastic, and may be in a shape other than tape, may be provided with button, fastener, magic tape, etc., and may be coated with a medical-grade adhesive agent on one face by which the tape is attached to the skin. Also, in the first embodiment, the sides of the dehiscence preventive member 1 are folded to form the double-layered parts to make the connection sides 3a, 3b, but it is possible to form the connection sides without doing anything particular to the sides of the dehiscence preventive member 1. It is only required that there be created a resultant function whereby the contraction distance in the dehiscence direction which is input accompanying the application of the dehiscence preventive member is rendered equal to or greater than the contraction distance in the dehiscence direction input accompanying the application of the holding members.

In the first embodiment, dehiscence preventive member 1, holding members 2a through 2l, and the connecting sides 3a, 3b are connected by sewing, but it is possible to adopt a method whereby there will be no stitches or seams throughout or at least a part of the aid. Incidentally, in the first embodiment of the inventive wound dehiscence preventive aid, the above-mentioned materials were used to make the respective members, but optionally acceptable materials include ones made of chemical fibers such as nylon, and natural fibers such as silk and flax; and preferred materials are those that provide the dehiscence preventive member 1, holding members 2a through 2l, and the connection sides 3a, 3b, respectively, with suitable breathability, flexibility, temperature-keeping effect, durability, etc. These are examples and are not the only choices. Furthermore, depending on the application, it is possible to use a plastic or a metal as the raw material, and also so long as it is suitable for medical use, any newly developed material can be used.

Furthermore, with regard to the material, shape, position, etc. of the holding members, there is no limitation or dependence on different applications so long as the resultant holding member is equipped with the function of holding the dehiscence preventive member closely on the wound and its surrounding tissues, and with the function of rendering the contraction distance of the dehiscence preventive member in the dehiscence direction input accompanying the application of the dehiscence preventive member equal to or greater than the contraction distance of the holding member in the dehiscence direction input accompanying the application of the holding member.

For example, it is possible to have an adhesive suitable for medical use constitute solely the holding member in a manner such that the adhesive is provided on a part of or all of the lower face of the dehiscence preventive member, and in this scenario it is preferable that the contraction distance of the holding member in the dehiscence direction input accompanying the application of the holding member is similar to that of the dehiscence preventive member in the dehiscence direction input accompanying the application of the dehiscence preventive member, it is possible that, depending on the shape of the dehiscence preventive member or of the holding member, difference between the contraction distance of the holding member in the dehiscence direction input accompanying the application of the holding member and the contraction distance of the dehiscence preventive member in the dehiscence direction input accompanying the application of the dehiscence preventive to member is small.

Next, Example 2 embodiment of the present invention based on a different dehiscence preventive aid will be explained with reference to FIGS. 3 through 5.

Figure 3:
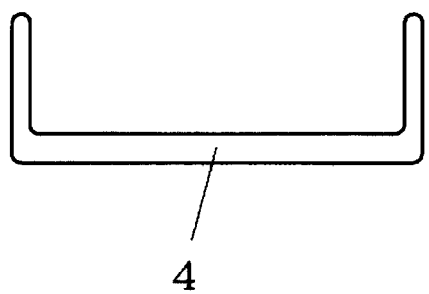
FIG. 3 is a schematic top plan view of a contraction preventive member to be equipped in an aid for prevention of wound dehiscence according to Example 2 of the present invention.
Figure 4:
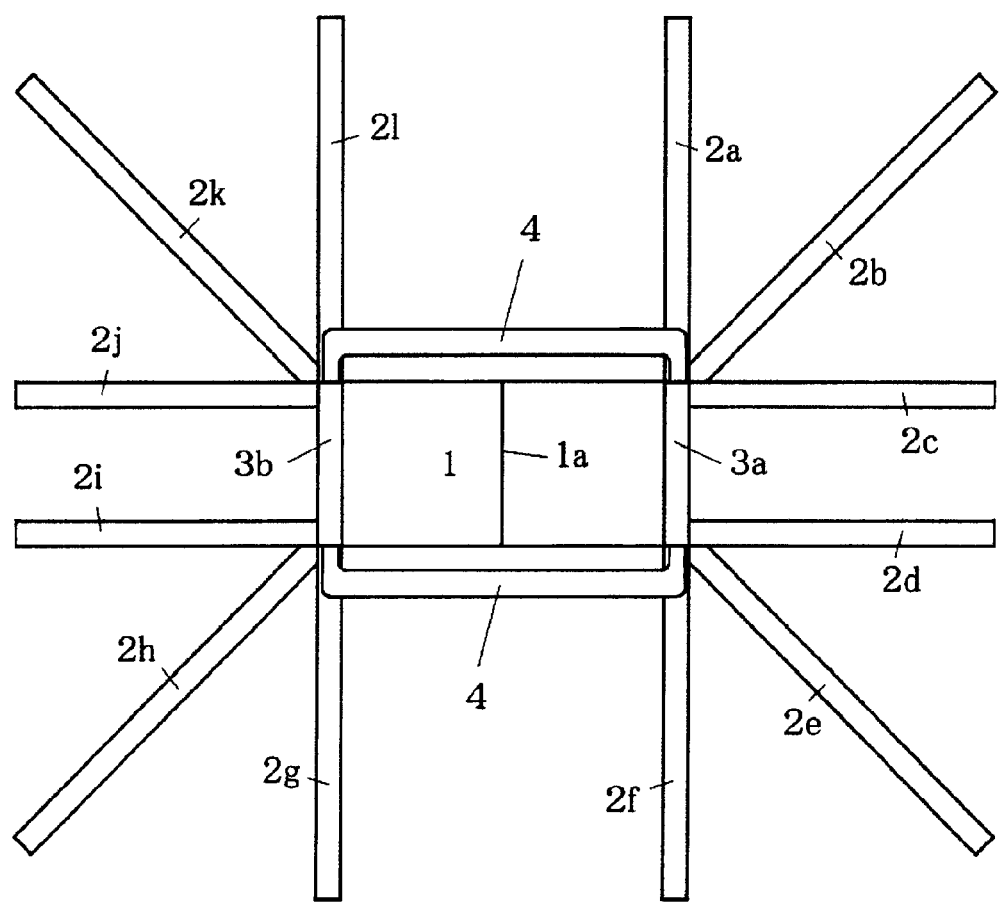
FIG. 4 is a schematic top plan view of an aid for prevention of wound dehiscence equipped with the contraction preventive member of FIG. 3, seen as of the time before being applied to the wound.

FIG. 3 is a schematic top plan view of a contraction preventive member 4, and FIG. 4 is a top plan view showing the front side of a wound dehiscence preventive aid equipped with the contraction preventive member 4 shown in FIG. 3 as of the time prior to the application. Incidentally, the numeral reference 1 designates a dehiscence preventive member, 1a the center line of the dehiscence preventive member 1, 2a, 2b, 2c, 2d, 2e, 2f, 2g, 2h, 2i, 2j, 2k, 2l the holding members, 3a, 3b the connection sides, and 4 the contraction preventive member.

In the wound dehiscence preventive aid of the Example 2 embodiment, the connecting sides 3a, 3b were made looped, and two of the metallic pieces shaped like a Japanese letter "コ", shown in FIG. 3, were used as the contraction preventive members 4, 4, and the legs of these were inserted into the looped connecting sides, a pair into the upper ends of the connection sides and the other pair into the lower ends of the connection sides, as shown in FIG. 4, whereby the dehiscence preventive member 1 is maintained in a state of appropriate expansion in the dehiscence direction, and thereby the contraction of the dehiscence preventive member 1 is checked, and the dehiscence preventive member 1 is held closely on the suture and the suture-surrounding skin, and the contraction preventive members 4 are removed when the application is completed with the holding members 2 (2a-2l) fitted to the body. Accordingly, it is possible to apply the dehiscence preventive aid easily with the dehiscence preventive member 1 in a state of expansion.

Figure 5:
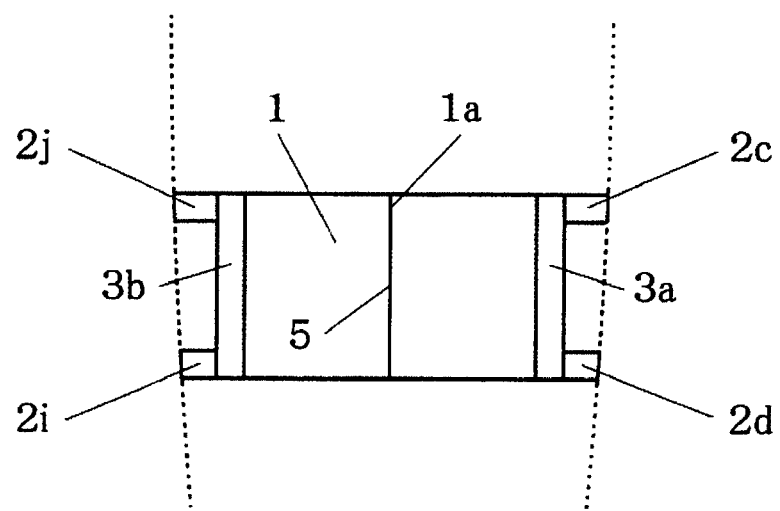
FIG. 5 is a schematic top plan view of the aid for prevention of wound dehiscence of FIG. 3, seen as of the time after it is applied to the wound.

FIG. 5 is a schematic top plan view of the wound dehiscence preventive aid shown in FIG. 4, after its application. In this figure, it is seen that a wound dehiscence preventive aid is applied with a center line 1a of the dehiscence preventive member coinciding with a suture 5 on an outside of a fore arm, and in order to distinguish the "wound dehiscence preventive aid" part from the "human body" part, the latter is drawn in broken line.

In Example 2 embodiment shown in FIG. 4, the dehiscence preventive member 1 was made of an elastic Bear Spandex Jersey (cotton 89%, polyurethane 11%), and was used in such a state that the contraction distance in the dehiscence direction input accompanying the application was greater than the contraction distance in the direction perpendicular to the dehiscence direction input accompanying the application, and that those sides of the dehiscence preventive member 1 which were perpendicular to the dehiscence direction were folded back double so as to create the tubular connection sides 3a, 3b. Also, the holding members 2a, 2b, 2c, 2d, 2e, 2f, 2g, 2h, 2i, 2j, 2k, 2l were made of twill fabric of cotton yarn which was not elastic, and were of lengths sufficient to suit for an application to a fore arm. The holding members 2a, 2b, 2c, 2d, 2e, 2f were sewn to the connection side 3a, and the holding members 2g, 2h, 2i, 2j, 2k, 2l were sewn to the connection side 3b. Furthermore, in the tubular connecting sides 3a, 3b were inserted from their ends two contraction preventive members 4 each consisting of a metal piece shaped like a staple or a Japanese letter "コ" shown in FIG. 3.

After application on a forearm, for example, the wound dehiscence preventive aid is, as shown in FIG. 5, fixed with appropriate holding means 2c, 2d, 2i, 2j mostly on the inner side of the forearm to thereby hold the dehiscence preventive member 1 closely on the suture and the suture-surrounding skin in such a manner that by virtue of the contractile force of the dehiscence preventive member 1 the aid functions to prevent dehiscence by trying to contract in the direction opposite to the dehiscence direction, and the unnecessary holding members 2a, 2b, 2e, 2f, 2g, 2h, 2k, 2l are seen to have been cut away. The contraction preventive members 4 are seen to be removed too from the tubular connecting sides 3a, 3b after the application. Preferably, the holding members are positioned in the dehiscence direction, and also are connected at the end portions of the connection sides of the dehiscence preventive member 1 so as to obtain closer holding of the dehiscence preventive member 1 onto the suture and the suture-surrounding skin; for example, when the suture 5 coincides with a center line 1a of the dehiscence preventive member 1, the holding members are preferably positioned where the holding members 2c, 2d, 2i, 2j are seen to be positioned in FIG. 5.

Also, in Example 2 embodiment, the connection sides 3a, 3b were made tubular and received staple-shaped metallic pieces as the contraction preventive member, but with regard to the material, shape, position, etc. of the contraction preventive member, there is no limitation or dependence on different applications so long as the contraction preventive member is equipped with the function of preserving the dehiscence preventive member in the appropriately expanded state.

The inventive wound dehiscence preventive aids shown in FIG. 1 and FIG. 2 are both equipped with the basic construction of the present invention, and by virtue of this construction, it is possible to incorporate into the dehiscence preventive aid a means for persistently reducing the physiological tension working on the tissues surrounding the wound, whereby by slackening the tissues surrounding the wound so as to create mild corrugation and to thereby persistently reduce the physiological tension working on the tissues surrounding the wound in the direction of dehiscence, it becomes possible to prevent the dehiscence caused by breaking of the suture thread after the suture or to prevent the dehiscence caused by the necrosis or the like of the tissues surrounding the sutured wound owing to the suture thread restricting the circulation.

Heretofore, we explained Example 1 and Example 2 embodiments of the inventive wound dehiscence preventive aid in the case of applying them to a sutured wound on the outer side of the fore arm, but it is possible to apply them to a wound irrespective of whether it is sutured or not. Also, it is possible to apply the inventive aid to any part of the body besides the outer side of the fore arm, after modifying the shape of the aid to suit the wounded part. Incidentally, what is meant, in this specification, by saying like "hold the dehiscence preventive member closely upon the tissues" is not only that the dehiscence preventive member is rendered in direct contact with the surface of the tissues but also that the dehiscence preventive member is rendered in indirect contact with the tissues with some treatment layer for optimizing the moist situation or Gauze, etc. interposed in-between to cover the tissues surrounding the wound. Furthermore, a similar result is also obtainable in a case where instead of suture thread a medical grade adhesive or a surgical staple or the like is used.

Furthermore, while the present invention proposes an aid for preventing wound dehiscence, which is highly effective in stopping the dehiscence of an incised wound, that is, an open wound caused when a part of the body is cut, and which is easy to handle and apply, the dehiscence preventive aid of the present invention is also useful in a case wherein, as described above, the dehiscence is caused by the necrosis of the tissues surrounding the sutured wound resulting from poor circulation of blood or the like and no good result is expected from re-suturing, and it is not a rare that the surgeon cannot help but resort to the classical remedy of removing all the sutured threads, excising the necrotic tissues, covering the wound with a wound dressing, and expecting for a natural healing. Furthermore, the inventive dehiscence preventive aid is expected to work well in preventing the dehiscence of other epithelium tissues as well as the skin, such as lip and nail. Therefore, the of the wound dehiscence preventive aid of the present invention is not limited to skin, but may be used on other epithelium tissues so long as it is medically effective. Also, it can be used irrespective of whether the wound is sutured or not.

INDUSTRIAL APPLICABILITY

The wound dehiscence preventive aid according to the present invention has extremely high effectiveness in preventing the dehiscence caused by physiological tension, and is useful irrespective of whether the wound is sutured or not, and is therefore highly contributory to the medical industry.

EXPLANATION OF REFERENCE NUMERALS

1: dehiscence preventive member
1a: center line of dehiscence preventive member
2: holding member
2a: holding member
2b: holding member
2c: holding member
2d: holding member
2f: holding member
2g: holding member
2h: holding member
2i: holding member
2j: holding member
2k: holding member
2l: holding member
3a: connection side
3b: connection side
4: contraction preventive member
5: suture

What is claimed is:

1. An aid for prevention of wound dehiscence for preventing an incised wound caused to a part of a body by incision from splitting open by covering the wound and wound-surrounding tissues, the aid comprising:
   a dehiscence preventive member adapted to cover up the wound and the wound-surrounding tissues;
   a holding member adapted to hold the dehiscence preventive member closely upon the wound and the wound-surrounding tissues; and
   a contraction preventive member having a capacity of keeping the dehiscence preventive member suitably expanded in a dehiscence direction and of preventing the expanded dehiscence preventive member from contracting, wherein
   a contraction distance of the dehiscence preventive member in the dehiscence direction which is determined in response to the application of the dehiscence preventive member is equal to or greater than a contraction distance of the holding member in the dehiscence direction which is determined in response to the application of the holding member,
   the dehiscence preventive member is adapted to be closely applied to the wound and the wound-surrounding tissues after being expanded in the dehiscence direction in a manner such that the contraction distance of the dehiscence preventive member in the dehiscence direction which is determined in response to the application of the dehiscence preventive member is equal to or greater than the contraction distance of the dehiscence preventive member in a direction normal to the dehiscence direction which is determined in response to the application of the dehiscence preventive member, and
   the contraction preventive member is removed after the dehiscence preventive member is applied by being fixed with the holding member.

2. An aid for prevention of wound dehiscence as claimed in claim 1 wherein the wound is sutured.

3. An aid for prevention of wound dehiscence as claimed in claim 1 wherein the wound is not sutured.

* * * * *